(12) United States Patent
Upasani et al.

(10) Patent No.: US 9,952,170 B2
(45) Date of Patent: Apr. 24, 2018

(54) METHODS AND SYSTEMS FOR MEASURING HOSE RESISTANCE

(75) Inventors: Sameer Subhash Upasani, Vadgaonsheri (IN); Abhay Shinde, Maharashtra (IN); Luis Pereira, Katy, TX (US)

(73) Assignee: Eaton Intelligent Power Limited, Dublin (IE)

( * ) Notice: Subject to any disclaimer, the term of this patent is extended or adjusted under 35 U.S.C. 154(b) by 58 days.

(21) Appl. No.: 14/396,286

(22) PCT Filed: Apr. 23, 2012

(86) PCT No.: PCT/IN2012/000296
§ 371 (c)(1),
(2), (4) Date: Feb. 9, 2015

(87) PCT Pub. No.: WO2013/160903
PCT Pub. Date: Oct. 31, 2013

(65) Prior Publication Data
US 2015/0177172 A1 Jun. 25, 2015

(51) Int. Cl.
*G01N 27/20* (2006.01)
*F16L 11/08* (2006.01)
(Continued)

(52) U.S. Cl.
CPC ............ *G01N 27/20* (2013.01); *F16L 11/086* (2013.01); *F16L 11/112* (2013.01); *F16L 11/127* (2013.01);
(Continued)

(58) Field of Classification Search
CPC ......... G01N 27/04; G01N 27/20; G01N 27/24
(Continued)

(56) References Cited

U.S. PATENT DOCUMENTS 2,291,070 A 7/1942 Bruno
2,436,949 A 3/1948 Anderson
(Continued)

FOREIGN PATENT DOCUMENTS

DE 31 40 804 A1 4/1983
DE 40 03 788 A1 8/1991
(Continued)

OTHER PUBLICATIONS

International Search Report for corresponding International Patent Application No. PCT/IN2012/000296 dated Nov. 27, 2012.
(Continued)

*Primary Examiner* — Walter L Lindsay, Jr.
*Assistant Examiner* — Milton Gonzalez
(74) *Attorney, Agent, or Firm* — Merchant & Gould P.C.

(57) ABSTRACT

Systems and methods for detecting degradation and failures, include types of failures, in a hose assembly are disclosed. One system includes a hose degradation monitoring circuit having a hose assembly including a hose having first and second conductive layers, and a degradation monitoring circuit configured to detect a resistance of the hose across the conductive layers. The degradation monitoring circuit includes a voltage source electrically connected to the first conductive layer, and a resistor electrically connected between the second conductive layer and ground. The degradation monitoring circuit further includes a voltage monitoring circuit electrically connected between the resistor and the second conductive layer, to periodically monitor a voltage at the location and detect a possible failure of the hose assembly upon determining that, based at least in part on a change in the voltage at the location over time, a resistance of the hose assembly has passed a threshold level.

16 Claims, 14 Drawing Sheets

(51) Int. Cl.

| | | |
|---|---|---|
| *F16L 11/127* | (2006.01) | |
| *F16L 25/01* | (2006.01) | |
| *F16L 33/207* | (2006.01) | |
| *G01N 27/04* | (2006.01) | |
| *G01M 5/00* | (2006.01) | |
| *F16L 11/112* | (2006.01) | |

(52) U.S. Cl.
 CPC ........... *F16L 25/01* (2013.01); *F16L 33/2076* (2013.01); *G01M 5/0025* (2013.01); *G01M 5/0083* (2013.01); *G01N 27/041* (2013.01)

(58) Field of Classification Search
 USPC .................................................. 324/691, 693
 See application file for complete search history.

(56) References Cited

U.S. PATENT DOCUMENTS

| | | | |
|---|---|---|---|
| 2,451,450 | A | 10/1948 | Spraragen |
| 4,029,889 | A | 6/1977 | Mizuochi |
| 4,229,613 | A | 10/1980 | Braun |
| 4,446,892 | A | 5/1984 | Maxwell |
| 5,102,012 | A | 4/1992 | Foster |
| 5,159,200 | A * | 10/1992 | Dunbar |
| 5,267,670 | A | 12/1993 | Foster |
| 5,343,738 | A | 9/1994 | Skaggs |
| 5,387,899 | A | 2/1995 | DiLauro et al. |
| 5,442,810 | A | 8/1995 | Jenquin |
| 5,551,484 | A | 9/1996 | Charboneau |
| 5,634,497 | A | 6/1997 | Neto |
| 5,671,689 | A | 9/1997 | Clapp et al. |
| 5,969,618 | A | 10/1999 | Redmond |
| 5,992,218 | A | 11/1999 | Tryba et al. |
| 6,384,611 | B1 * | 5/2002 | Wallace |
| 6,386,237 | B1 | 5/2002 | Chevalier et al. |
| 6,498,991 | B1 | 12/2002 | Phelan et al. |
| 6,735,705 | B1 | 5/2004 | Egbert et al. |
| 6,958,615 | B2 | 10/2005 | Poulbot et al. |
| 7,555,936 | B2 | 7/2009 | Deckland |
| 8,087,430 | B1 | 1/2012 | Betz et al. |
| 8,183,872 | B2 | 5/2012 | Stark |
| 8,217,669 | B1 | 7/2012 | Watkins, Jr. |
| 8,515,687 | B2 | 8/2013 | Pereira et al. |
| 8,829,929 | B1 | 9/2014 | Watkns, Jr. |
| 8,997,792 | B2 | 4/2015 | Betsinger et al. |
| 2001/0018845 | A1 | 9/2001 | Roberts |
| 2002/0154029 | A1 | 10/2002 | Watters et al. |
| 2003/0164048 | A1 | 9/2003 | Shkel |
| 2004/0065377 | A1 | 4/2004 | Whiteley |
| 2005/0253821 | A1* | 11/2005 | Roeder |
| 2006/0196252 | A1 | 9/2006 | Deckland |
| 2006/0196722 | A1* | 9/2006 | Makabe ............... B62D 5/0481 180/443 |
| 2006/0226701 | A1 | 10/2006 | Gatz et al. |
| 2007/0051166 | A1 | 3/2007 | Baker et al. |
| 2007/0131035 | A1 | 6/2007 | Krutz et al. |
| 2008/0036617 | A1 | 2/2008 | Arms et al. |
| 2009/0042419 | A1 | 2/2009 | Palomo |
| 2010/0007325 | A1 | 1/2010 | Stark |
| 2010/0174495 | A1 | 7/2010 | Pereira et al. |
| 2010/0308575 | A1 | 12/2010 | Rodenburg |
| 2011/0152024 | A1 | 6/2011 | Kuehl |
| 2011/0226302 | A1 | 9/2011 | Farmer et al. |
| 2011/0281488 | A1 | 11/2011 | Li |
| 2012/0136592 | A1 | 5/2012 | Pereira et al. |
| 2012/0204923 | A1 | 8/2012 | Ortiz et al. |
| 2012/0278018 | A1 | 11/2012 | Hastreiter |
| 2013/0134992 | A1* | 5/2013 | Zhu |
| 2014/0076449 | A1 | 3/2014 | Betsinger et al. |
| 2014/0238109 | A1 | 8/2014 | Wells et al. |
| 2014/0265561 | A1 | 9/2014 | Beining |
| 2015/0240972 | A1 | 8/2015 | Betsinger |
| 2015/0300538 | A1 | 10/2015 | Al-Atat et al. |

FOREIGN PATENT DOCUMENTS

| | | | |
|---|---|---|---|
| EP | 1 126 205 | A1 | 8/2001 |
| EP | 1 722 217 | A1 | 11/2006 |
| EP | 2 261 546 | A1 | 12/2010 |
| GB | 1574749 | A * | 9/1980 |
| JP | 2011027216 | A * | 2/2011 |
| WO | WO 03/079749 | A2 | 10/2003 |
| WO | WO 2008/001238 | A2 | 1/2008 |
| WO | WO 2008/059226 | A2 | 5/2008 |
| WO | 2011/143384 | A1 | 11/2011 |
| WO | WO 2012/012482 | A1 | 1/2012 |
| WO | WO 2012/071424 | A2 | 5/2012 |
| WO | WO 2012/149161 | A1 | 11/2012 |

OTHER PUBLICATIONS

Holland, Z. et al., "Layered Polymer Whole Structure Health Monitoring Using Capacitance Sensing", *IEEE/ASME International Conference on Advanced Intelligent Mechatronics*, Montreal, Canada, Jul. 6-9, 2010, pp. 943-946.

European Search Report for Application No. 12875245.8 dated Dec. 15, 2015.

ISR & Written Opinion for PCT/US2011/061865 dated May 21, 2012, 12 pages.

ISR & Written Opinion for PCT/US2012/035216 dated Jul. 16, 2012, 14 pages.

ISR & Written Opinion for PCT/US2014/017590 dated Jun. 3, 2014, 11 pages.

ISR for PCT/US2013/059465 dated Dec. 3, 2013, 3 pages.

ISR & Written Opinion for PCT/US2013/059473 dated Jul. 18, 2014, 15 pages.

Invitation to Pay Addt'l Fees w/Partial Is for PCT/US2013/059473 dated Feb. 28, 2014, 6 pages.

ISR & Written Opinion for PCT/US2014/029286 dated Jun. 18, 2014, 13 pages.

Radtke et al., Design of Power-Transmitting Hydraulic Hose with Integrated Controller Area Network and Life-Sensing Capability, 2005 Agricultural Equipment Technology Conference, Feb. 15, 2005.

Hewlett Packard Technical Manual, printed Apr. 24, 2003, 8 Pages.

International Search Report for Application No. PCT/US2013/030966 dated Aug. 1, 2013.

Invitation to Pay Additional Fees with Partial International Search for Application No. PCT/US2013/048660 dated Mar. 24, 2014.

International Search Report and Written Opinion for Application No. PCT/US2013/048660 dated Sep. 8, 2014.

Guo, Z. et al., "GRE: Graded Residual Energy Based Lifetime Prolonging Algorithm for Pipeline Monitoring Sensor", *9th International Conference on Parallel and Distributed Computing Applications and Technologies*, 203-210 (2008).

Mohamed, M. et al., "Power Harvesting for Smart Sensor Networks in Monitoring Water Distribution System", *International Conference on Networking, Sensing and Control*, 393-398 (2011).

Ok, C. et al., "Optimal Transmission Power in Self-sustainable Sensor Networks for Pipeline Monitoring", *IEEE International Conference on Automation Science and Engineering*, 591-596 (2007).

* cited by examiner

METHODS AND SYSTEMS FOR MEASURING HOSE RESISTANCE

This application is a National Stage Application of PCT/IN2012/000296, filed 23 Apr. 2012, and which application is incorporated herein by reference. To the extent appropriate, a claim of priority is made to the above disclosed application.

TECHNICAL FIELD

The present disclosure relates to methods and systems for measuring hose resistance, for example to detect failures in a hose.

BACKGROUND

High pressure reinforced hydraulic hose is typically used on a variety of fluid power operated machines, such as earth-moving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube.

Many applications are demanding hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance.

To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

In some circumstances, it is desirable to detect, in a non-destructive and non-disruptive manner a likelihood of failure of a hydraulic hose. One solution providing this capability is discussed in U.S. Pat. No. 7,555,936, and discloses connecting a monitor circuit between two parallel, at least partially-conductive layers of a hose wall. A change in an electrical property observed by that monitor circuit may indicate a change in a property of the hose wall structure that might indicate impending failure of the hose wall. However, even with this solution, it can be difficult to determine whether the changed electrical property is in fact due to a change in a physical feature of a hose wall, or if the changed electrical property is due to a change in the sensing electronics, a change in an electrical property of a harness connecting the monitoring circuit to the hose wall, or simply degradation of an electrical connection to the hose wall. In these cases, there may be a change in an electrical property observed, even when hose wall integrity is not compromised, but instead is due to a change in position or pressure within the hose. Accordingly, existing arrangements might not adequately detect degradation or failure of a hose, but instead may attribute some other type of positional or pressure change of the hose as degradation or failure. Additionally, it is difficult to determine the type of failure that may (or may not) be occurring.

SUMMARY

An aspect of the present disclosure relates to a hose degradation monitoring system that includes a hose assembly including a hose having a first conductive layer and a second conductive layer, and a degradation monitoring circuit configured to detect a resistance of the hose across the first and second conductive layers. The degradation monitoring circuit includes a voltage source electrically connected to the first conductive layer and a resistor electrically connected between the second conductive layer and a ground. The degradation monitoring circuit also includes a voltage monitoring circuit electrically connected to a location between the resistor and the second conductive layer, the voltage monitoring circuit configured to periodically monitor a voltage at the location and detect a possible failure of the hose assembly upon determining that, based at least in part on a change in the voltage at the location over time, a resistance of the hose assembly has passed a threshold level.

A second aspect of the present disclosure relates to a method of monitoring degradation of a hose assembly having concentric first and second conductive layers separated by an insulating layer. The method includes applying a voltage to the first conductive layer and measuring a voltage and a current across a resistor connected between the second conductive layer and a ground. The method also includes determining a resistance attributable to the hose assembly based on the voltage and current measured across the resistor, and comparing the resistance to a threshold resistance value. The method further includes, based at least in part on a determination that the resistance falls below the threshold resistance, generating an indication of degradation of the hose assembly.

A third aspect of the present disclosure relates to a method of detecting a type of failure of a hose assembly. The method includes periodically applying a voltage to a first conductive layer of a hose assembly including first and second conductive layers, and upon applying the voltage to the first conductive layer, measuring a voltage and a current across a resistor connected between the second conductive layer and a ground. The method includes determining a resistance attributable to the hose assembly based at least in part on the voltage as measured between the second conductive layer and a ground, and from each resistance, computing an admittance of the hose assembly. The method further includes, based at least in part on changes to the computed admittance of the hose assembly, determining the existence of a failure in the hose assembly.

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

In general, the present disclosure relates generally to methods and systems for measuring hose resistance, for example to detect failures in a hose. In various embodiments discussed below in connection with the associated Figures, resistance measurements, and other related measurements are taken relative to a particular hose that has two or more conductive layers. Methods of scaling those measurements to detect when failures in the hose are about to occur or have occurred are disclosed as well, are disclosed, in which circuits are implemented that can determine various types of errors based on analysis of rate of change of electrical characteristics of the hose. Using the methods and systems as discussed herein, various types of hose degradation and failure can be detected and distinguished from one another.

Figure 1:
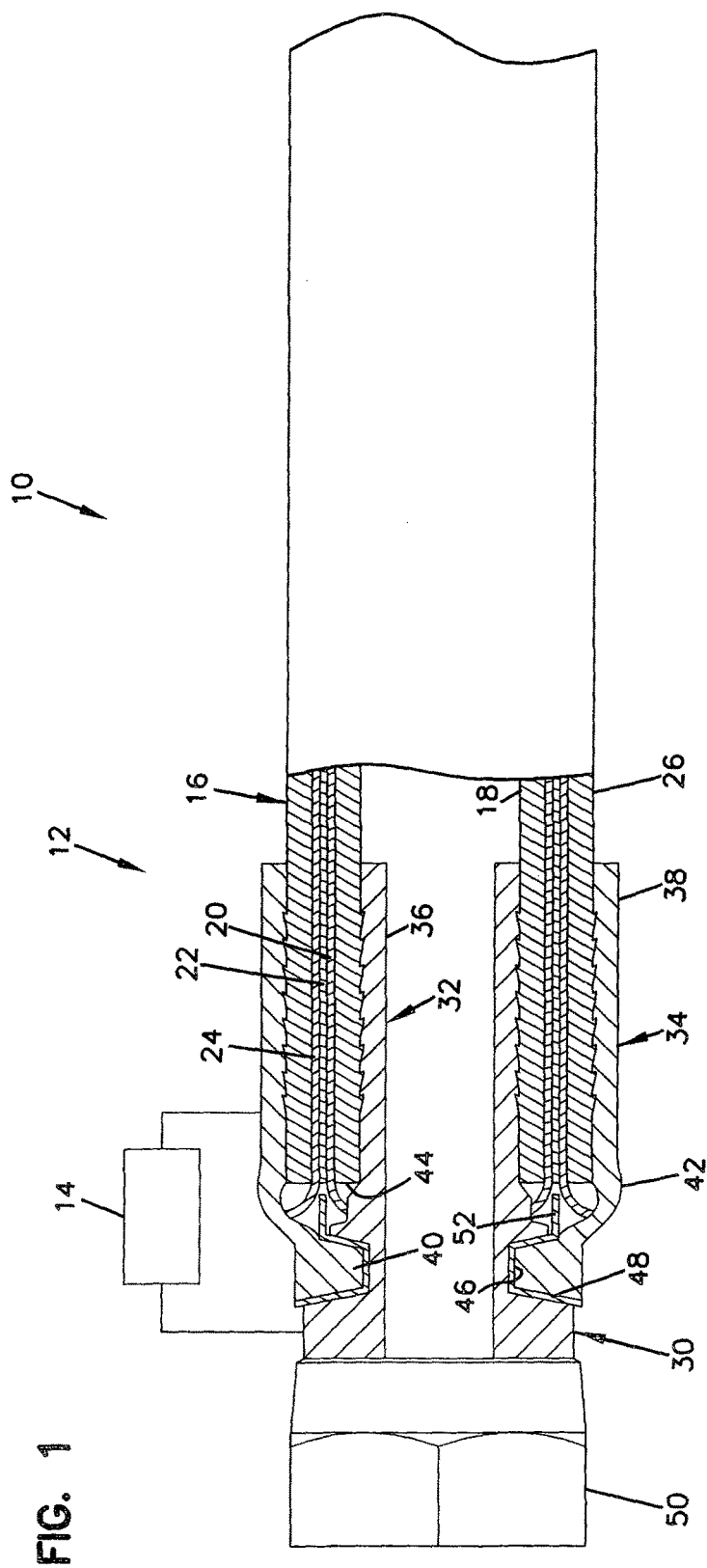
FIG. 1 is a partial cross-sectional view of an exemplary hose assembly employing a fault detector having exemplary features of aspects in accordance with the principles of the present disclosure.

Referring now to FIG. 1, an exemplary hose fault detection system, generally designated 10, is shown. The hose fault detection system 10 includes a hose assembly, generally designated 12, and optionally a monitoring assembly 14 in electrical and physical communication with the hose assembly 12.

The hose assembly 12 includes a hose, generally designated 16, having a multi-layer construction. In the subject embodiment, the hose 16 is generally flexible and includes an inner tube 18 made from a polymeric material, such as rubber or plastic, or another material depending on the requirements of the particular application, a first conductive layer 20, an intermediate layer 22, a second conductive layer 24 and an outer cover 26. The first and second conductive layers 20, 24 define an electrical characteristic of the hose assembly 12, such as capacitance, inductance and/or resistance (impedance).

In the subject embodiment, the first conductive layer 20 overlays the inner tube 18 and the intermediate layer 22 overlays the first conductive layer 20. The second conductive layer 24 overlays the intermediate layer 22. The first and second conductive layers 20, 24 may be configured as reinforcing layers. The outer cover 26 may overlay the second conductive layer 24, and may include, for example, an extruded layer of rubber or plastic. The outer cover 26 may itself include a reinforcing layer.

The intermediate layer 22 operates to at least partially insulate electrically the first and second conductive layers 20, 24 from one another. The intermediate layer 22 may have any of a variety of constructions. For example, the intermediate layer 22 may consist of a single layer of an electrically resistive material. The intermediate layer 22 may also consist of multiple layers, wherein at least one of the layers exhibits electrical insulating properties. Certain composite materials may also be employed in the intermediate layer 22, such as a woven fabric bonded to a polymeric material. Composite materials having various other constructions may also be utilized. Composite materials may also be used in combination with other materials to form the intermediate layer 22.

The first and second conductive layers 20, 24 generally extend the entire length and span the entire circumference of the hose. This is generally the case when the conductive layer also functions as a reinforcement layer. The intermediate layer 22 may also extend over the entire length and circumference of the hose. There may be instances, however, where at least one of the first and second conductive layers 20, 24 extends only over a portion of the hose length and/or a portion of its circumference. In that instance, the intermediate layer 22 may also be configured to generally extend over the region of the hose containing the partial conductive layer 20, 24. The partial intermediate layer 22 may be positioned within the hose so as to separate the first and second conductive layers 20, 24 from one another.

Figure 2:
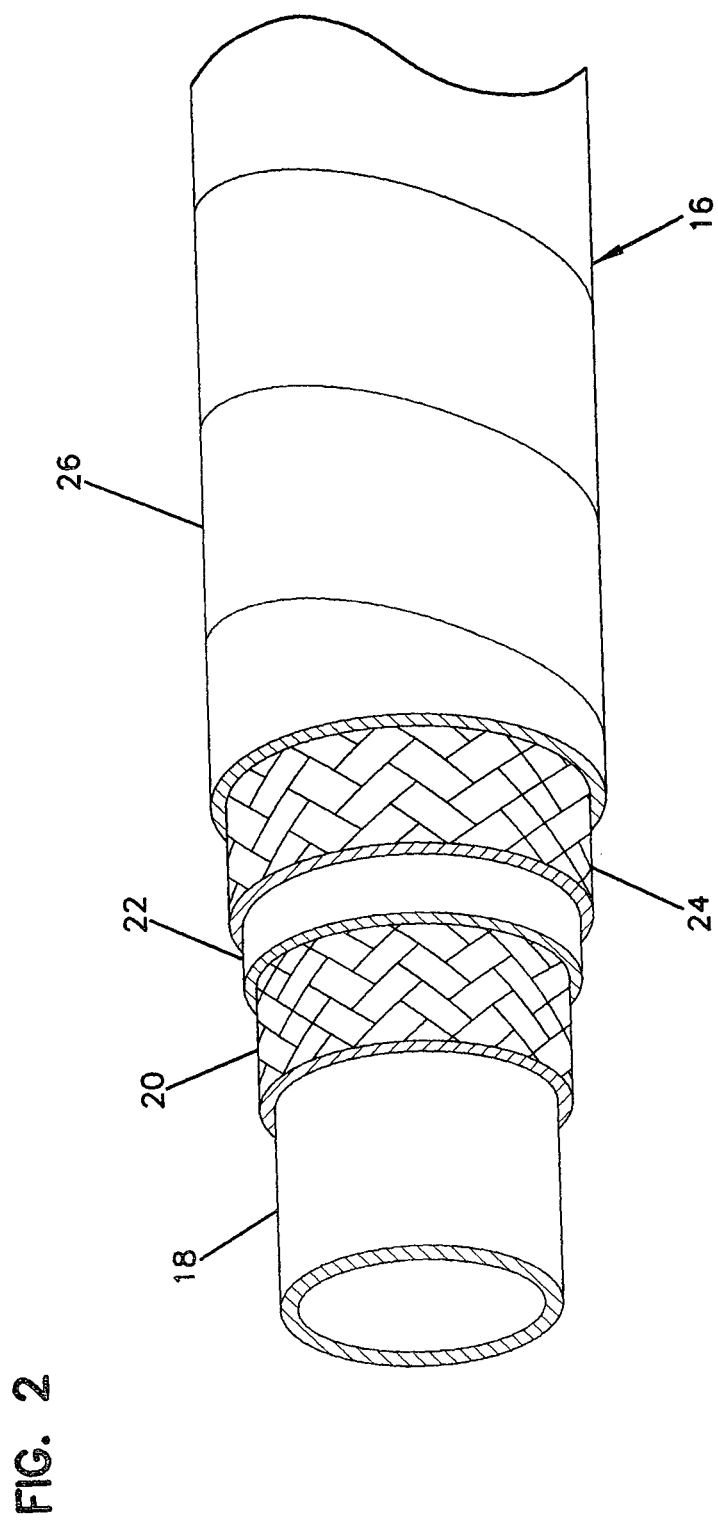
FIG. 2 is a perspective view, partially cut away, illustrating an exemplary hose employing a braided conductive layer that is suitable for use with the hose assembly of FIG. 1.
Figure 3:
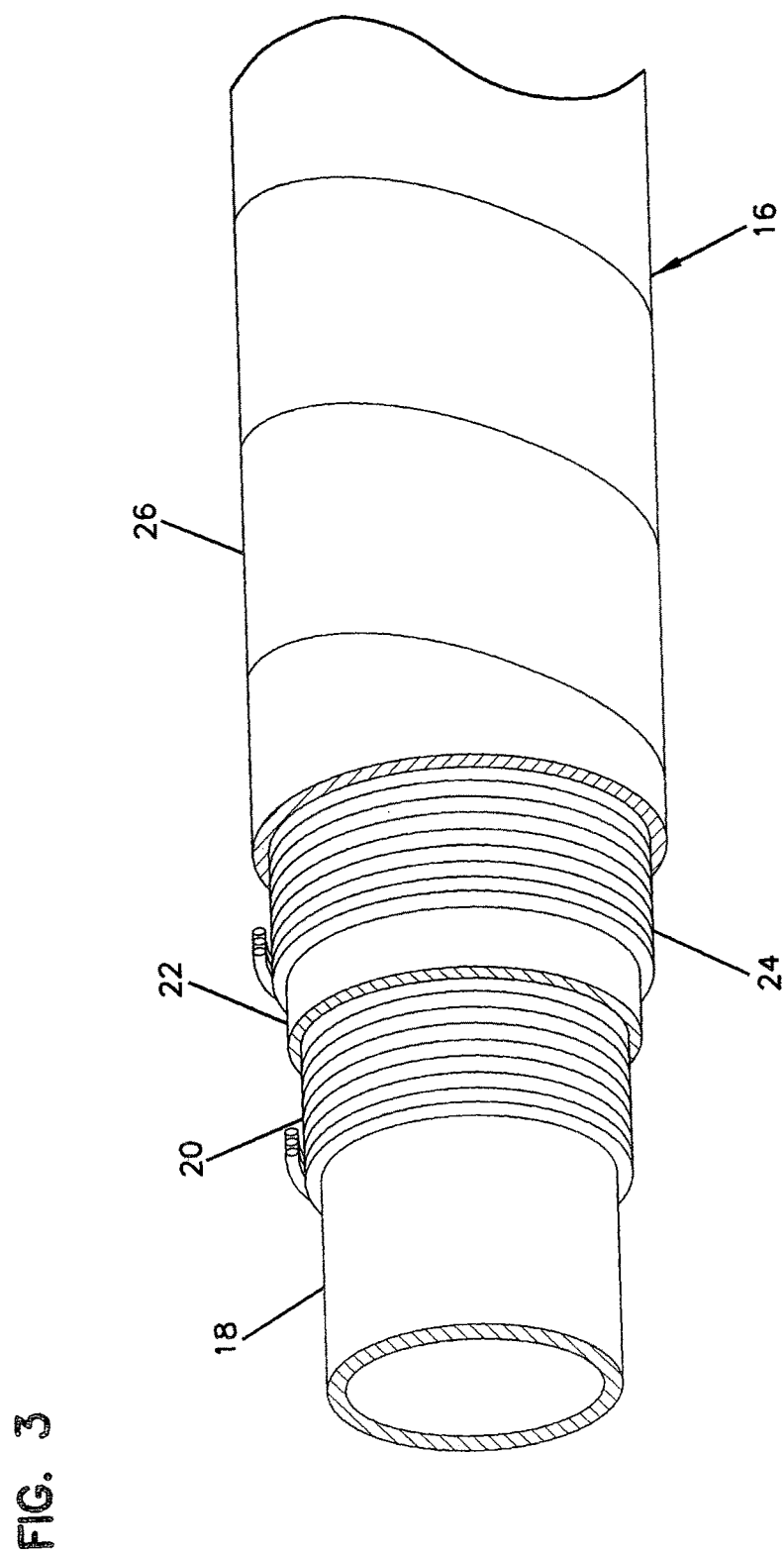
FIG. 3 is a perspective view, partially cut away, illustrating an exemplary hose employing a spiral wire conducting layer that is suitable for use with the hose assembly of FIG. 1.

Referring now to FIGS. 2 and 3, the first and second conductive layers 20, 24 may include, for example, an electrically conductive braided reinforcement material, such as shown in FIG. 2, or alternating layers of electrically conductive spiral reinforcement material, such as shown in FIG. 3. The braided reinforcement material may consist of a single layer or may include multiple layers. Although a two-wire spiral reinforcement arrangement is depicted in FIG. 3, it shall also be appreciated that other configurations, such as four and six wire arrangements, may also be utilized.

The first and second conductive layers 20, 24 may each have the same configuration, or each layer may be configured differently. For example, the first and second conductive layers 20, 24 may each include the braided material shown in FIG. 2, or one of the first and second conductive layers 20, 24 may include the braided material while the other of the first and second conductive layers 20, 24 may include the spiral reinforcement material shown in FIG. 3. Additionally, the first and second conductive layers 20, 24 may include a single ply or multiple plies of reinforcement material. The first and second conductive layers 20, 24 may comprise metal wire, natural or synthetic fibers and textiles, and other reinforcement materials, provided the selected material is electrically conductive.

Referring again to FIG. 1, the hose assembly 12 may include a hose fitting, generally designated 30, for fluidly coupling the hose 16 to another component. The hose fitting 30 may have any of a variety of different configurations depending, at least in part, on the requirements of the particular application.

In the subject embodiment, the hose fitting 30 includes a nipple, generally designated 32, that engages the inside of the hose 16 and a socket, generally designated 34, that engages the outside of the hose 16. The nipple 32 includes an elongated cylindrical end portion 36 that engages the inner tube 18 of the hose 16. A cylindrically shaped end portion 38 of the socket 34 engages the outer cover of the hose 16. The socket 34 and nipple 32 may be constructed from an electrically conductive material.

The socket 34 and nipple 32 can be secured to the hose 16 by crimping the end portion 38 of the socket 34 overlaying the hose 16. The crimping process deforms the end portion 38 of the socket 34, thereby compressing the hose 16 between the nipple 32 and the socket 34. In the subject embodiment, the portions of the nipple 32 and the socket 34 that engage the hose 16 include a series of serrations that at least partially embed into the relatively softer hose material when the socket 34 is crimped to help secure the hose fitting 30 to the hose 16. The serrations may be configured to prevent the serrations from penetrating the inner tube and outer cover and contacting the first and second conductive layers 20, 24.

In the subject embodiment, the socket 34 includes an inwardly extending circumferential lug 40 positioned near an end 42 of the socket 34 adjacent an end 44 of the hose 16. The lug 40 engages a corresponding circumferential slot 46 formed in the nipple 32 for securing the socket 34 to the nipple 32. The end 42 of the socket 34 having the lug 40 is initially formed larger than the nipple 32 to enable the socket 34 to be assembled onto the nipple 32. During the assembly process the end 42 of the socket 34 is crimped, which deforms the socket 34 and forces the lug 40 into engagement with the corresponding slot 46 in the nipple 32. The socket 34 can be electrically insulated from the nipple 32 by positioning an electrically insulating collar 48 between the socket 34 and nipple 32 at the point the lug 40 engages the slot 46.

The hose fitting 30 also includes a nut 50 rotatably attached to the nipple 32. The nut 50 provides a means for securing the hose assembly 12 to another component.

The first conductive layer 20 may be configured to extend beyond the end of the inner tube of the hose 16. The first conductive layer 20 may engage the nipple 32 to create an electrical connection between the nipple 32 and the first conductive layer 20. Similarly, the second conductive layer 24 may be configured to extend beyond an end of the outer cover of the hose 16. The second conductive layer 24 may engage the socket 34 to create an electrical connection between the socket 34 and the second conductive layer 24.

To help prevent the portions of the first and second conductive layers 20, 24 that extend beyond the end of the hose 16 from contacting one another, an electrically insulating spacer 52 may be positioned between the exposed ends of the first and second conductive layers 20, 24. The spacer 52 may be integrally formed as part of the collar 48 used to electrically insulate the socket 34 from the nipple 32.

The spacer 52 may also be formed by extending the intermediate layer 22 of the hose 16 beyond an end of the inner tube 18 and outer cover 26. The spacer 52 may also be configured as a stand alone component separate from the collar 48 and the intermediate layer 22 of the hose 16.

The monitoring assembly 14 may have any of a variety of configurations. In general, the monitoring assembly 14 is connectable over a portion of the hose assembly 12, in particular the portion illustrated in FIG. 1. The monitoring assembly 14, when installed over hose assembly 12, forms a physical and electrical connection with the hose assembly 12, and in particular to nipple 32 and socket 34, respectively. In some embodiments, the monitoring assembly 14 includes a monitoring circuit, such as those described below. Generally, the monitoring assembly 14 detects an electrical characteristic of the hose assembly 12, while validating the connection to the nipple 32 and socket 34. An exemplary monitoring assembly 14 is described in further detail below, in connection with FIGS. 4-9.

Figure 4:
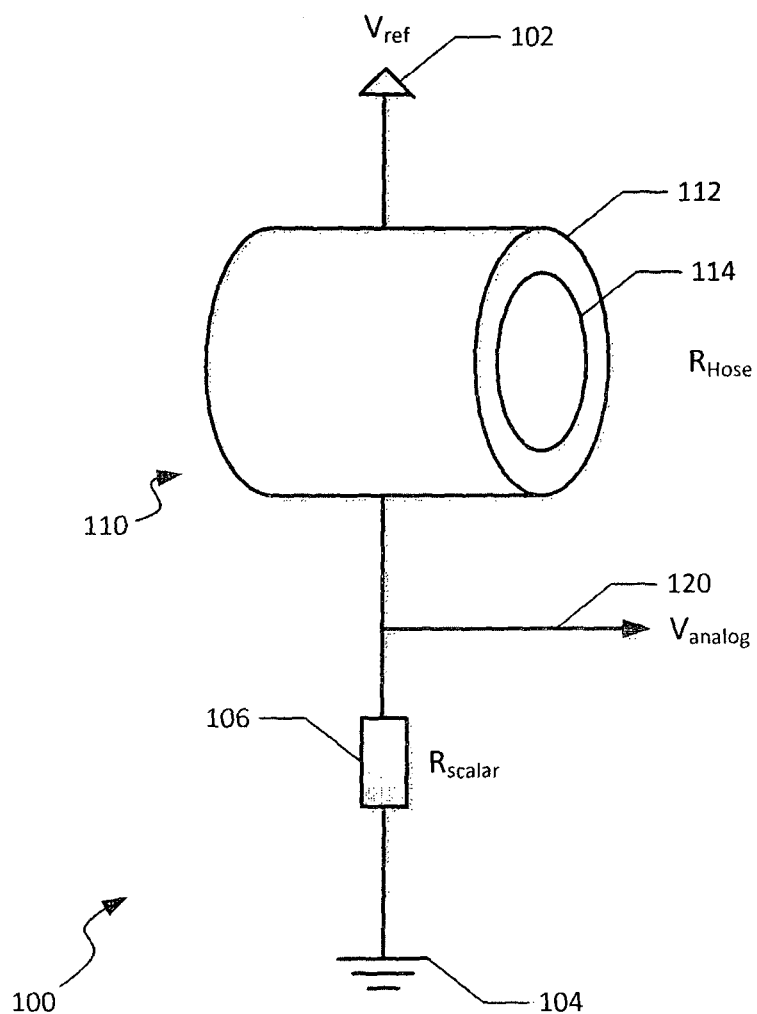
FIG. 4 is a generalized schematic view of a monitoring circuit useable with the hose assembly of FIGS. 1-3 to provide adaptive scaling of a hose resistance measurement to detect failure or degradation of a hose assembly, according to a possible embodiment of the present disclosure.

Referring now to FIGS. 4-9, systems and methods for monitoring a hose assembly are illustrated, including circuits that can be included in a monitoring assembly 14 as described above in connection with FIG. 1. FIG. 4 is a schematic view of a monitoring circuit 100 that can be used within a monitoring assembly 14. The monitoring circuit includes a voltage source 102 and ground 104, as well as a resistor 106 (labeled as $R_{scalar}$). In this embodiment, the voltage source 102 connects to a first conductive layer 112 of a hose assembly 110 having first and second conductive layers 112, 114 (e.g., corresponding to layers 20, 24), via an exposed connection location (e.g., nipple 32 and socket 34). The second conductive layer 114 is then electrically connected to the resistor 106, which is in turn connected to ground 104. In some embodiments, such as that shown in FIG. 8, below, the voltage source 102 is a known constant direct current voltage, referred to as $V_{ref}$. For example, the voltage source 102 and ground 104 could represent opposite ends of a battery, which can selectively be applied across the hose assembly.

To monitor the hose assembly, voltage and current passing through the circuit 100 can be measured. In the embodiment shown, a voltage ($V_{analog}$) 120 is measured by a voltage monitoring circuit. The voltage 120 represents a voltage divider between the hose assembly 110 and the resistor 106. By determining the voltage and current at this location within the circuit, it is possible to determine an overall resistance of the circuit (based on a known overall voltage $V_{ref}$). This can be done using variations on a voltage divider equation, as follows:

$$V_{analog} = V_{ref} \times (R_{scalar}/R_{hose} + R_{scalar})$$

In various embodiments of the present disclosure, different values can be used for the voltage source 102 and resistor 106. However, it is generally recognized that although a "good" hose may have a resistance ($R_{hose}$) that varies widely, a failing hose will have a decreased resistance value. For example, a "good" or newly manufactured hose may have a resistance anywhere from about 10 kΩ to about 1 MΩ. Hence, in some embodiments, it can be advantageous to select a value for the resistor 106 that maximizes a change in the voltage 120 for changes in resistance of the hose assembly 110 at relatively low resistance values, to ensure that even small changes in resistance of the hose assembly are detected. Additionally, as the resistance of the hose decreases, any current passing through the circuit 100 will increase, as illustrated in the following current equation:

$$I_{circuit} = V_{ref}/(R_{hose} + R_{scalar})$$

Accordingly, it would be advantageous, from a power savings perspective, to maintain a relatively high resistance, to ensure that even in a worst case scenario (i.e., a short circuit formed between hose layers), the maximum current passing through the circuit 100 would be $V_{ref}/R_{scalar}$.

Figure 5:
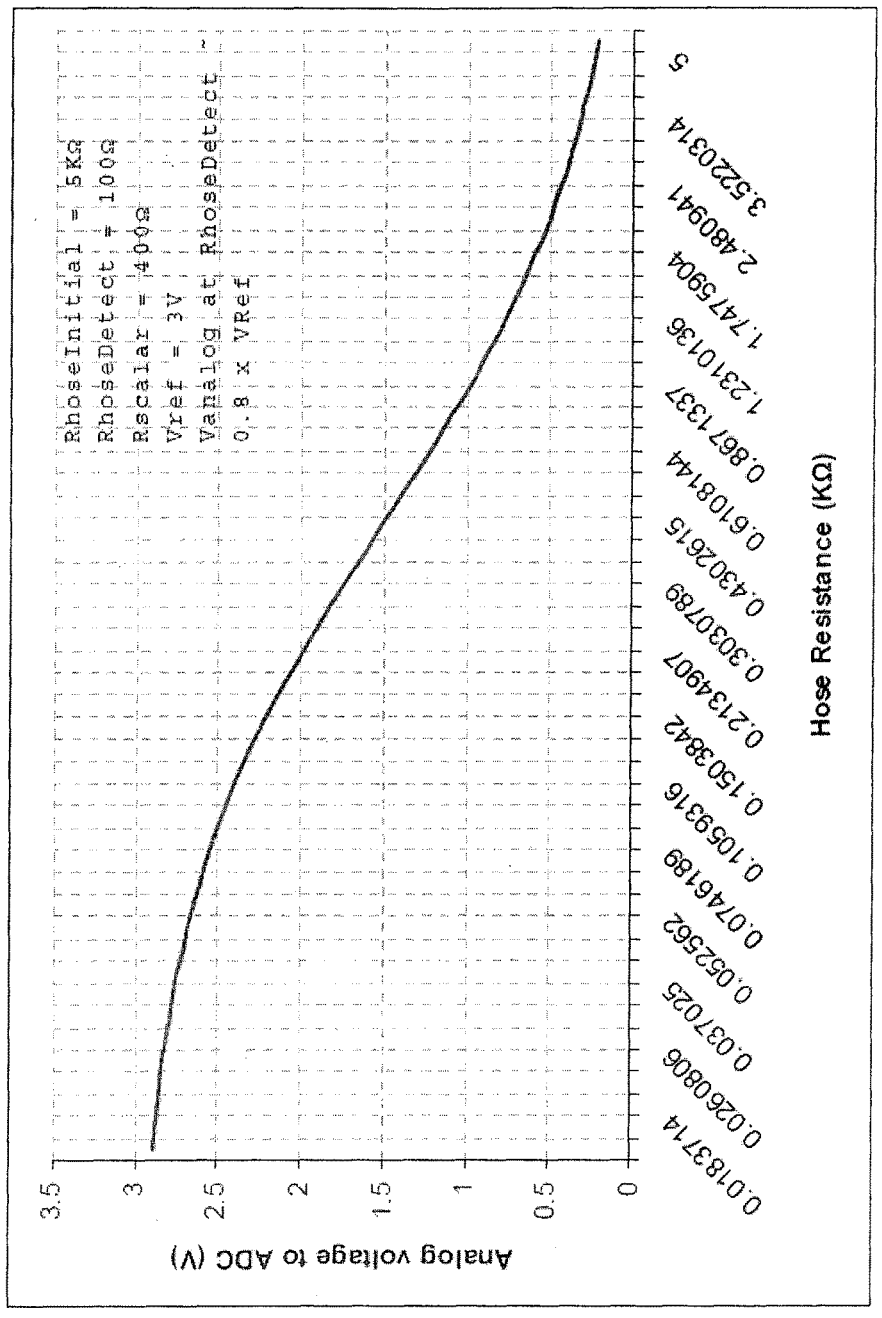
FIG. 5 is a chart illustrating a first set of experimental results indicating a range of voltages and associated resistive values observed when using the monitoring circuit illustrated in FIG. 4.
Figure 6:
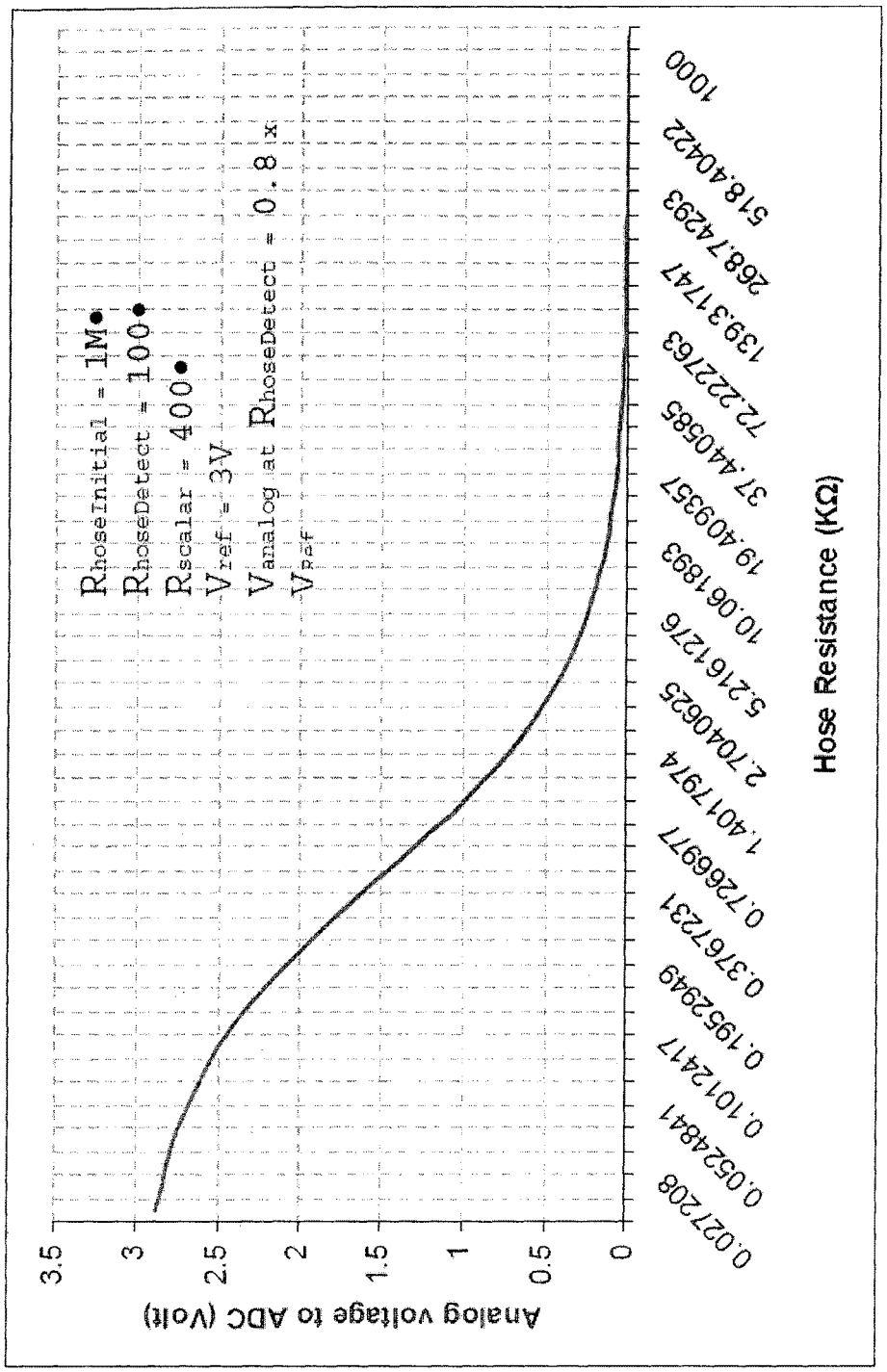
FIG. 6 is a chart illustrating a second set of experimental results indicating a range of voltages and associated resistive values observed when using the monitoring circuit illustrated in FIG. 4.

Referring now to FIGS. 5-6, and continuing the discussion of circuit values in the monitoring circuit 100, charts are illustrated which show a voltage-resistance relationship using examples at opposite ends of the spectrum of expected hose assembly resistances. In FIG. 5, a chart 200 is shown that illustrates the voltage-resistance relationship in a "low resistance" example. In this example, a tested "good" hose assembly in this arrangement is determined to have an initial resistance $R_{hose}$ of 5 kiloohms (kΩ). In this arrangement, a 400 Ohm (Ω) resistor is selected as resistor 106, and a 3 Volt reference voltage is selected for the voltage source 102. Because it has been empirically determined that a failed hose typically has a resistance below about 100 ohms (Ω), as a hose degrades and eventually fails, the hose resistance $R_{hose}$ will drop, causing the voltage 120 to rise as the scalar resistor 106 ($R_{scalar}$) begins to dominate the voltage divider equation. As such, for resistances below about 100 Ohms, the voltage $V_{analog}$ will rise to about 80% or greater of the total voltage provided by the voltage source $V_{ref}$. However, during normal operation, the hose resistance will remain high, keeping the voltage 120 $V_{analog}$ a low proportion of the overall source voltage 102 $V_{ref}$.

In FIG. 6, a chart 300 illustrates the voltage-resistance relationship in a "high resistance" example. In this example, a tested "good" hose assembly in this arrangement is determined to have an initial resistance $R_{hose}$ of 1 megaohm (MΩ). In this arrangement, a 400 Ohm (Ω) resistor is again selected as resistor 106, and a 3 Volt reference voltage is selected for the voltage source 102. Again, because it has been empirically determined that a failed hose typically has a resistance below about 100 ohms (Ω), as a hose degrades and eventually fails, the voltage $V_{analog}$ will rise to about 80% or greater of the total voltage provided by the voltage source $V_{ref}$ in case of a hose assembly failure.

In alternative arrangements, for example if hose failures were determined to result in observing a higher resistive value, a larger value may be used for resistor 106 in the circuit 100. By altering the value of resistor 106, it is possible to alter the threshold at which hose degradation or likely failure can be detected. For example, use of a larger resistor 106 could allow for increased sensitivity to changes in hose resistance near that larger value. Or, if hose resistance can drop well below 100 Ohms without affecting the hose continuity or operation, a smaller resistor 106 could be used. However, it is understood that in the case of a smaller resistor, greater currents will be experienced. For example, in a worst case of hose failure (i.e., a hose having a resistance below about 100 Ohms), the greatest resistance would be about 0.75 mA, with a more typical value being about 0.6 mA at a point of failure.

Figure 7:
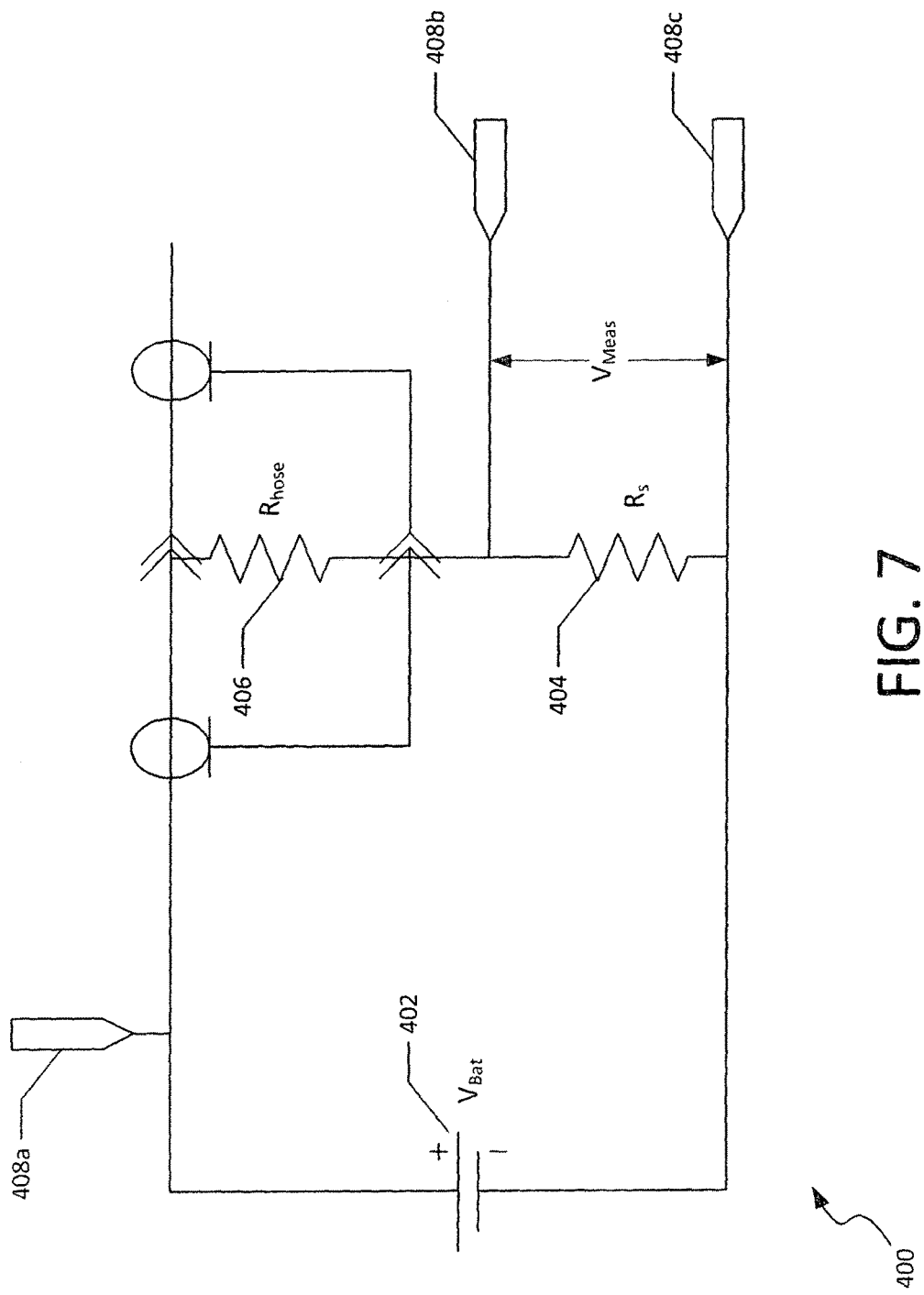
FIG. 7 is a generalized schematic view of a monitoring circuit useable with the hose assembly of FIGS. 1-3 to provide adaptive scaling of a hose resistance measurement to detect failure or degradation of a hose assembly, according to a second possible embodiment of the present disclosure.

Referring now to FIG. 7, an alternative monitoring circuit 400 is illustrated which can be used to detect degradation or failure in a hose assembly, such as that shown in FIGS. 1-3, above. The monitoring circuit 400 in this embodiment is configured to be connected to a data acquisition device, such as a microprocessor or microcontroller, which can be used to monitor and track voltage and current measurements over time to determine a typical degradation of a hose over time. In this embodiment, the circuit 400 includes a voltage source, shown as a battery 402 ($V_{bat}$). As with the circuit 100 illustrated in FIG. 4, the circuit 400 includes a scalar resistor 404 ($R_{scalar}$). In this embodiment, the hose assembly is modeled as a set of parallel resistors, which combined to form an equivalent hose resistor 406 ($R_{hose}$). Data access points 408a-c allow a remote data acquisition system (not shown) to monitor a positive voltage level (at data access point 408a), an analog voltage point at $V_{meas}$ (at data access point 408b) and a local ground (at data access point 408c). Using differences between signal levels at each point, it is possible to monitor a relationship between the voltage across the entire circuit ($V_{bat}$) and the voltage drop across the resistor 404, as well as the current passing through the circuit (I) to determine hose resistance ($R_{hose}$).

Optionally, the circuit 400 can also include a switch controllable by the data acquisition system or a remote system to periodically connect the battery 402 to the rest of circuit 400, thereby limiting the amount of time the overall circuit is connected and limiting the rate of discharge of the battery.

The data acquisition device can take any of a variety of forms, and can include a voltage monitoring circuit for determining a voltage $V_{meas}$. The data acquisition device could be a programmable circuit integrated with the circuit 400, or a separate/remote computing system. Such a device could include, for example, one or more programmable circuits having general purpose analog I/O connections.

Figure 8:
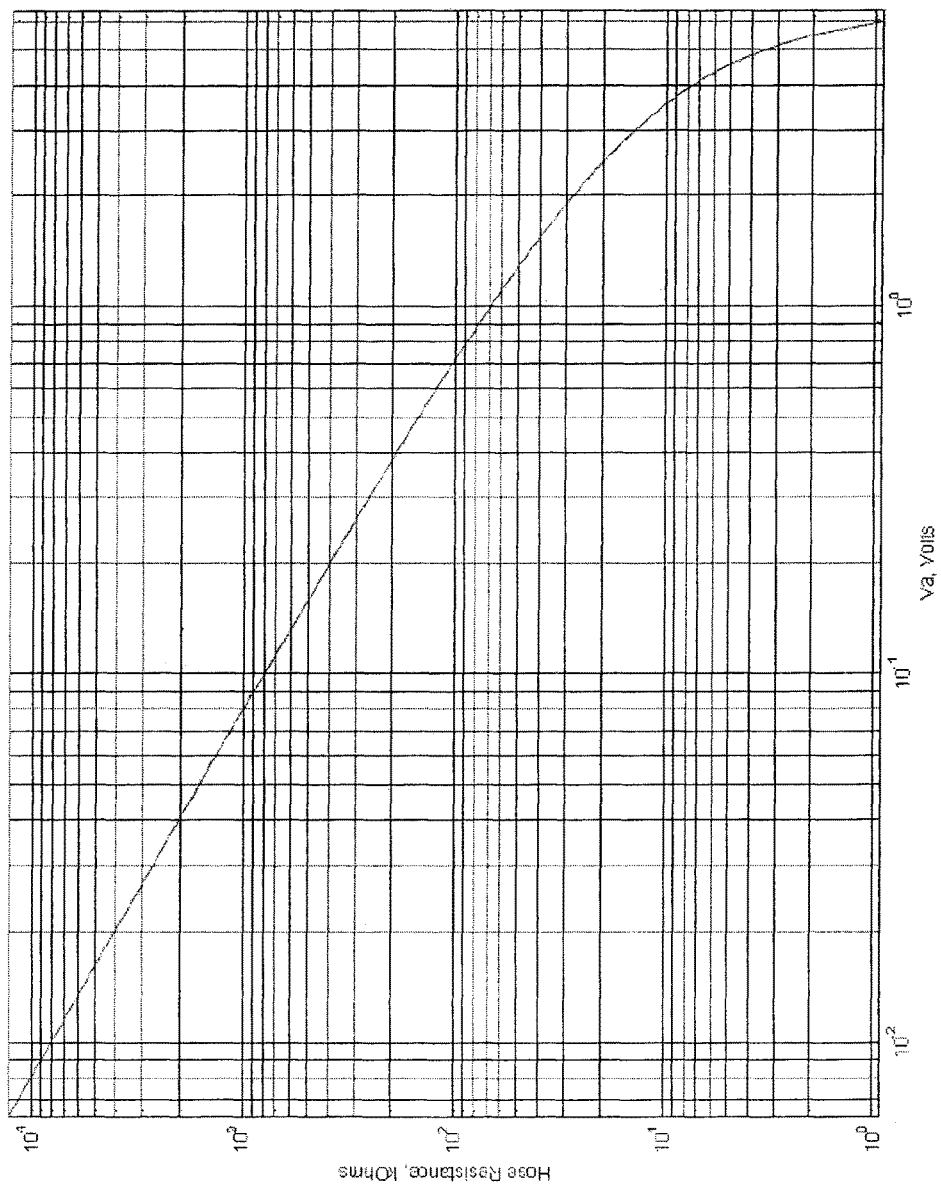
FIG. 8 is a log-scale chart illustrating voltage and resistance values in a circuit such as the one shown in FIG. 4.

Referring now to FIG. 8, an example chart 500 of results from a test of the circuit illustrated in FIG. 7 is shown. In the chart 500, a relationship between hose resistance ($R_{hose}$) and the measurement voltage ($V_{meas}$) is illustrated. The chart 500 was meas. developed using a source voltage of 6.33 V and a scalar resistor of 12.85 kOhms. The intent in selecting such values was to utilize a maximum of 0.5 mA current during any given test to provide acceptable battery life, and to plot the $V_{meas}$ voltage versus the hose resistance $R_{hose}$. In this example, it can be seen that as the hose resistance decreases, the measured voltage increases at a constant rate until the hose resistance approaches the scalar resistance, at which time smaller changes in hose resistance result in smaller changes in voltage, meaning that the effect of the scalar resistor $R_{scalar}$ dominates the voltage divider circuit.

Figure 9:
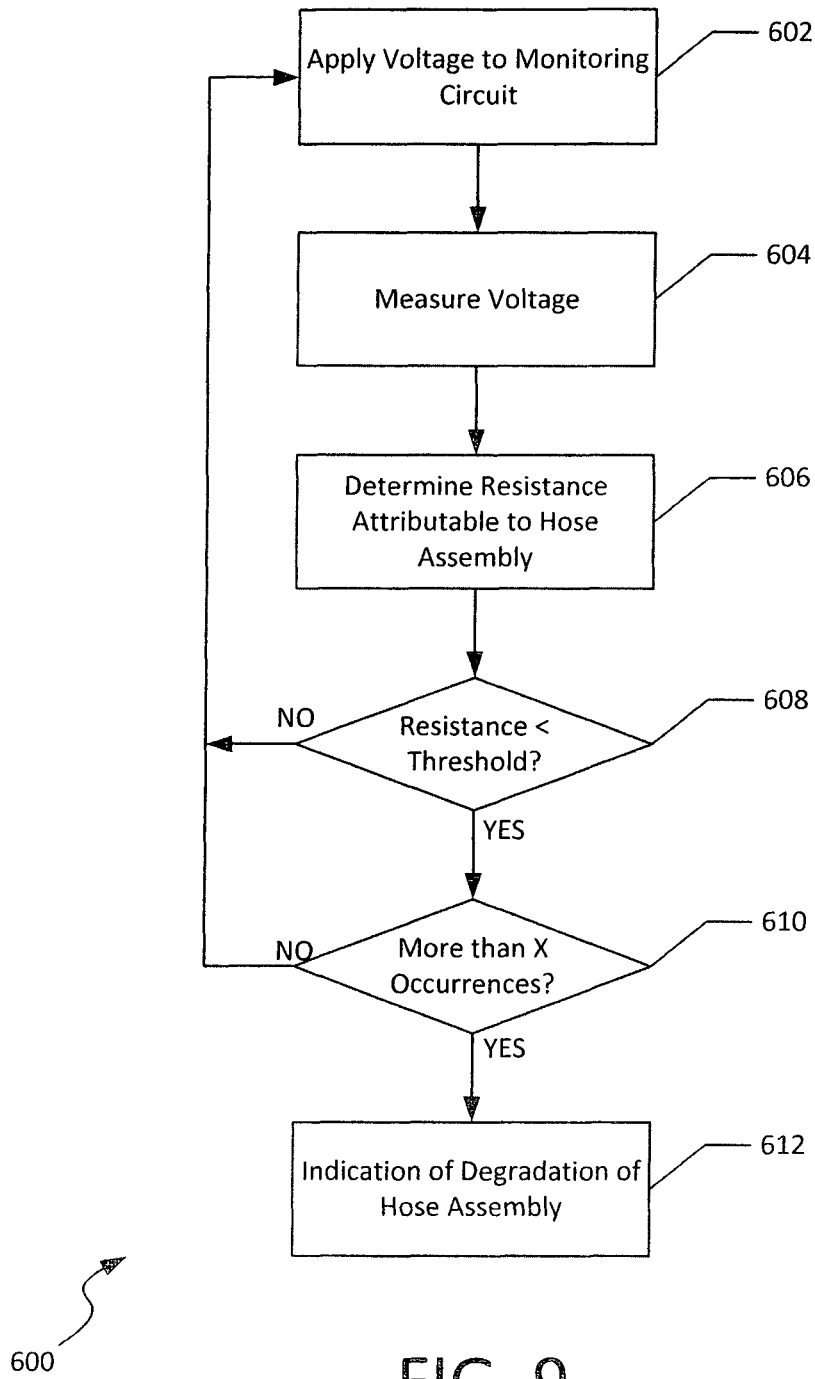
FIG. 9 is a flowchart of a method for monitoring degradation of a hose assembly, according to an example embodiment.

Referring now to FIG. 9, a flowchart of a method 600 for monitoring degradation of a hose assembly, according to an example embodiment. The method 600 can be performed periodically, for example by using a programmable circuit or other computing system or data acquisition device interfaced to a monitoring circuit such as those shown in FIGS. 4 and 7.

The method 600 includes applying a voltage to a monitoring circuit, for example by applying a battery across a monitoring circuit as illustrated in FIG. 7 (step 602). The method includes measuring a voltage at a position between the hose assembly and a scalar resistor, as well as optionally determining a current across the overall circuit (step 604). The method includes determining a resistance attributable to the hose assembly (step 606), and comparing that resistance to a predetermined threshold resistance below which it is assumed that the hose has degraded or failed (step 608). If the resistance is not below the threshold resistance, the method 600 includes periodically repeating this monitoring process. However, if the resistance is below the threshold resistance, this may be due to a variance in operating conditions or other temporary event. Accordingly, a history tracking operation takes place to determine whether a sufficient number of comparisons between the hose resistance and the predetermined threshold resistance indicate that the condition is not temporary, but instead represents a current state of the hose (step 610). In example embodiments, this can take place within a microcontroller or other data acquisition device. If such a predetermined number of measurements has not yet occurred, operation returns to step 602 for continued monitoring of the hose assembly on a periodic basis. If that number of measurements has taken place, an alert or other indication of degradation of the hose assembly can be generated (step 612), and optionally communicated to a remote system or locally to notify a user that the hose should be replaced.

Referring generally to the methods and systems of FIGS. 4-9, it can be seen that by using a carefully selected scaling mechanism, including a scaling resistor, it is possible to ensure that in the range of hose resistances where failures are expected, even small changes in resistance result in relatively large changes in voltage, making it straightforward to detect degradation of a hose. Furthermore, using the methods and systems described in FIGS. 4-9, various types of degradation can be detected, as discussed below.

Referring now to FIGS. 10-13, schematic models of a hose assembly are shown, alongside example ways that such hose assemblies typically fail. It is recognized that, by detecting changes in hose characteristics using a modification on the above resistive measurements, different types of hose failures (e.g., internal failures vs. external failures) can be detected and distinguished from one another, for example by using the periodic resistance measurements discussed above with respect to FIGS. 4-9.

Figure 10:
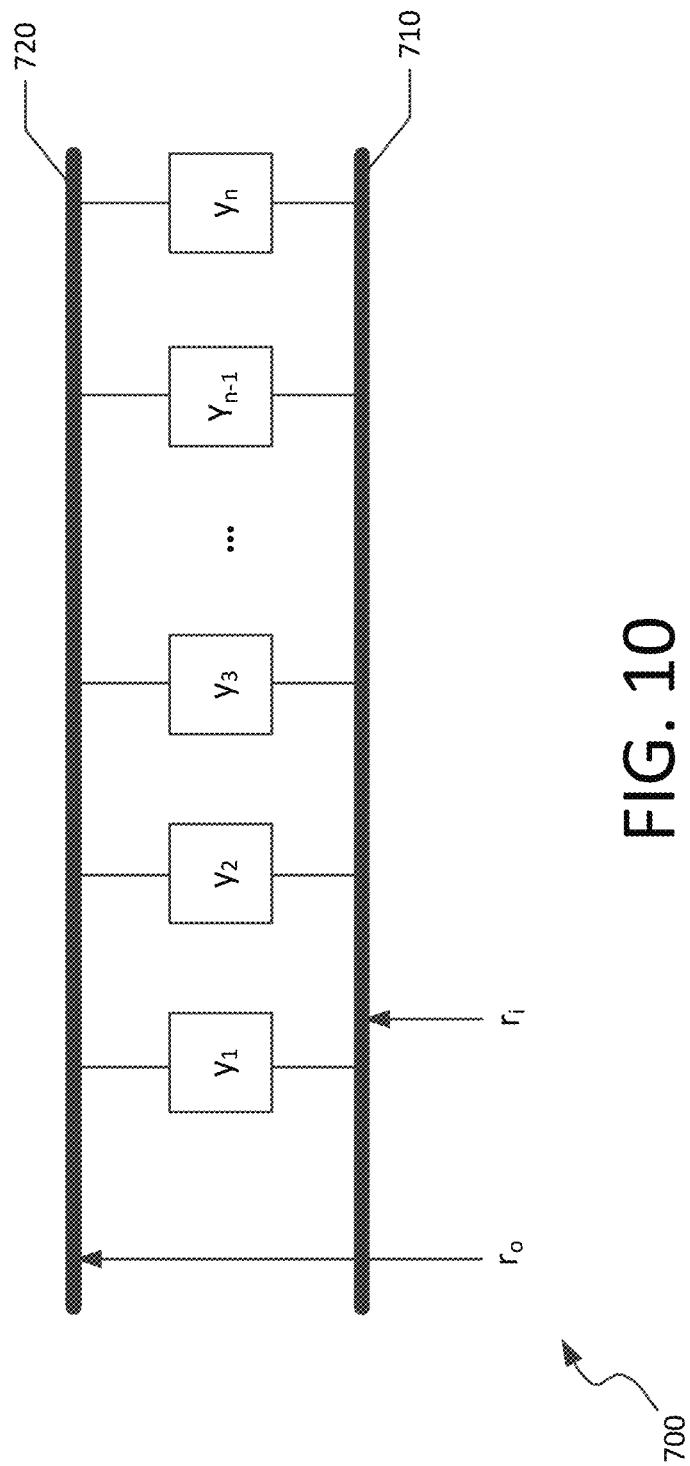
FIG. 10 is a schematic view of the hose assembly of FIGS. 1-3 as a set of parallel admittances, according to a possible embodiment of the present disclosure.

FIG. 10 illustrates an example schematic of a segment of a hose assembly 700 including inner and outer conductive layers 710, 720. When a potential difference is applied across the conductive layers 710, 720, that hose assembly will exhibit some resistance, as described above. However, as further described above, the resistance that appears to be a single resistance representing the hose overall in fact can also be represented as a number of parallel resistors and associated capacitances. Accordingly, if those parallel resistors are viewed in terms of the per unit length conductance, that conductance can be determined between the layers 710, 720 is known, and can be represented as:

$$G=k1/(\ln r_o - \ln r_i)$$

Similarly, the per-unit capacitance of the hose assembly per unit length can be represented as:

$$C=k2/(\ln r_o - \ln r_i)$$

In these equations, k1 and k2 are constants that can be determined and may vary based on the exact materials from which the hose assembly is constructed. And $r_o$ and $r_i$ are the outer and inner radii of the hose assembly.

To consider both conductance and capacitance on a per-unit basis as an aggregate effect, the hose can be viewed as having a per-unit length admittance y. As shown in FIG. 10, each unit length of the hose assembly 700 has an associated admittance $y_{1-n}$ associated therewith. Each local admittance value can be expressed as:

$$y_i = \text{length} * k/(\ln r_o - \ln r_i)$$

A total admittance can be calculated or modeled as the sum of each of these local admittances.

Figure 11:
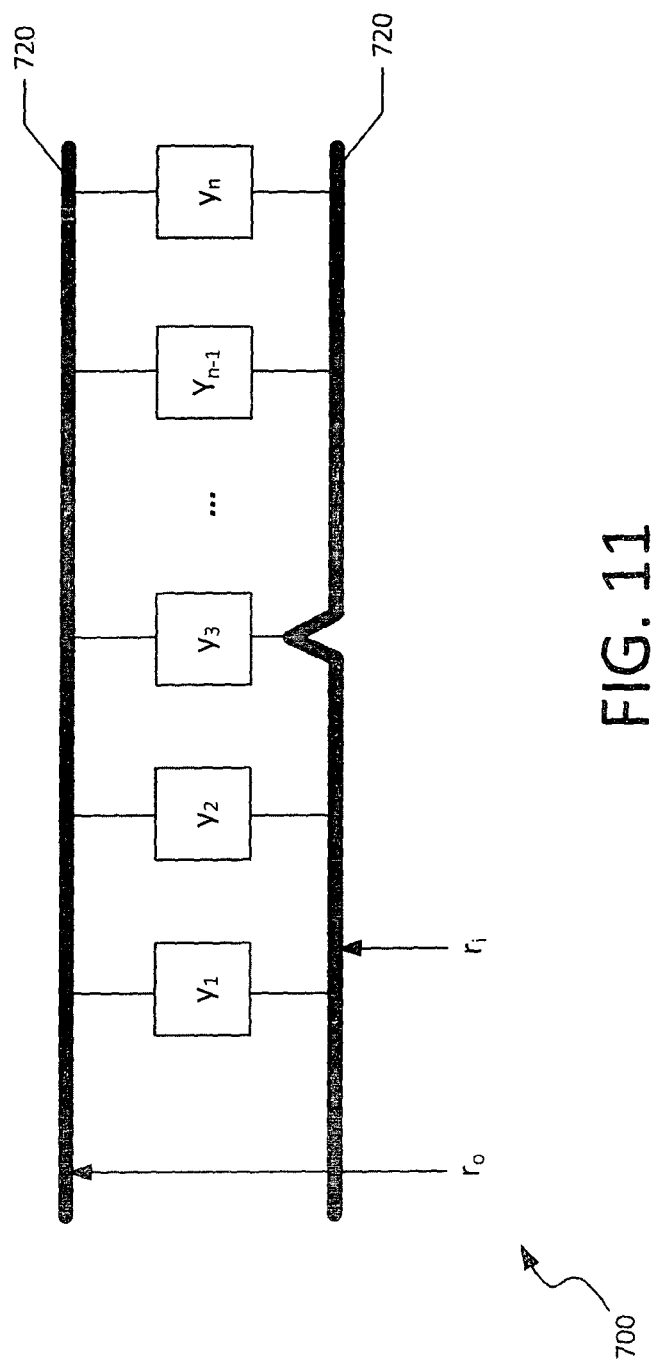
FIG. 11 is a schematic view of the hose assembly of FIG. 10 including an internal hose failure.
Figure 12:
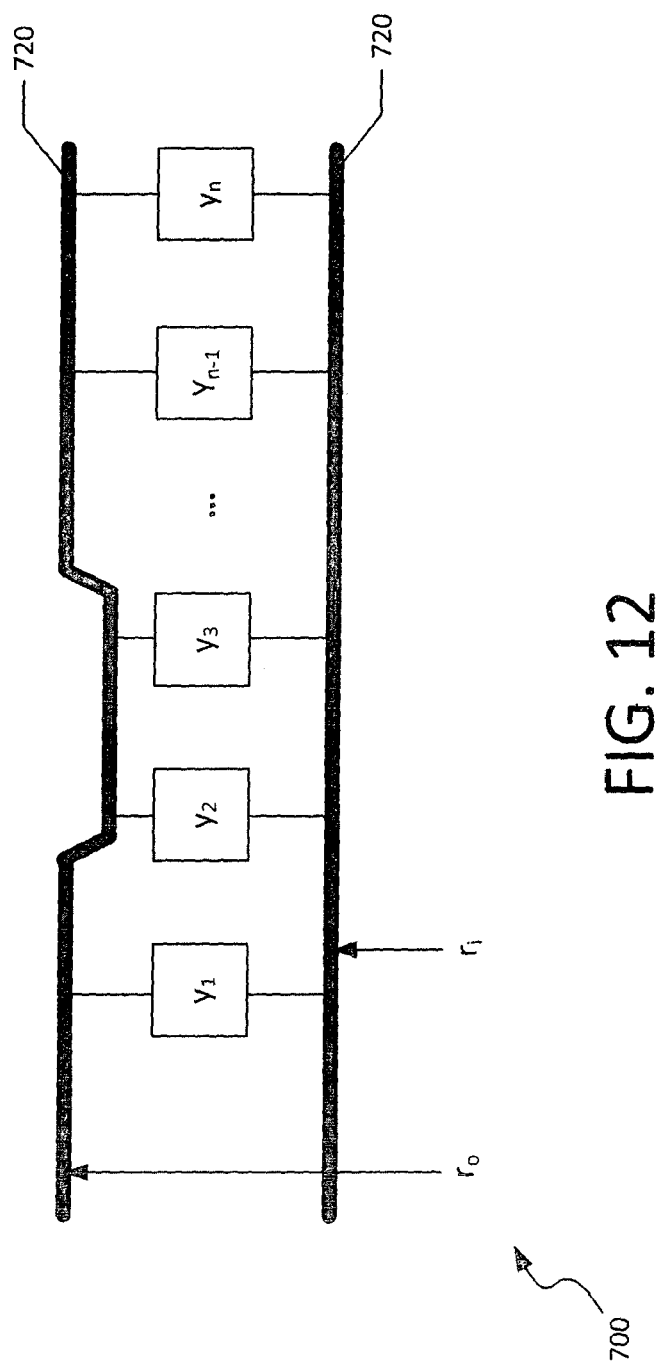
FIG. 12 is a schematic view of the hose assembly of FIG. 10 with external pressure applied to the hose assembly at a particular location, according to an example embodiment.
Figure 13:
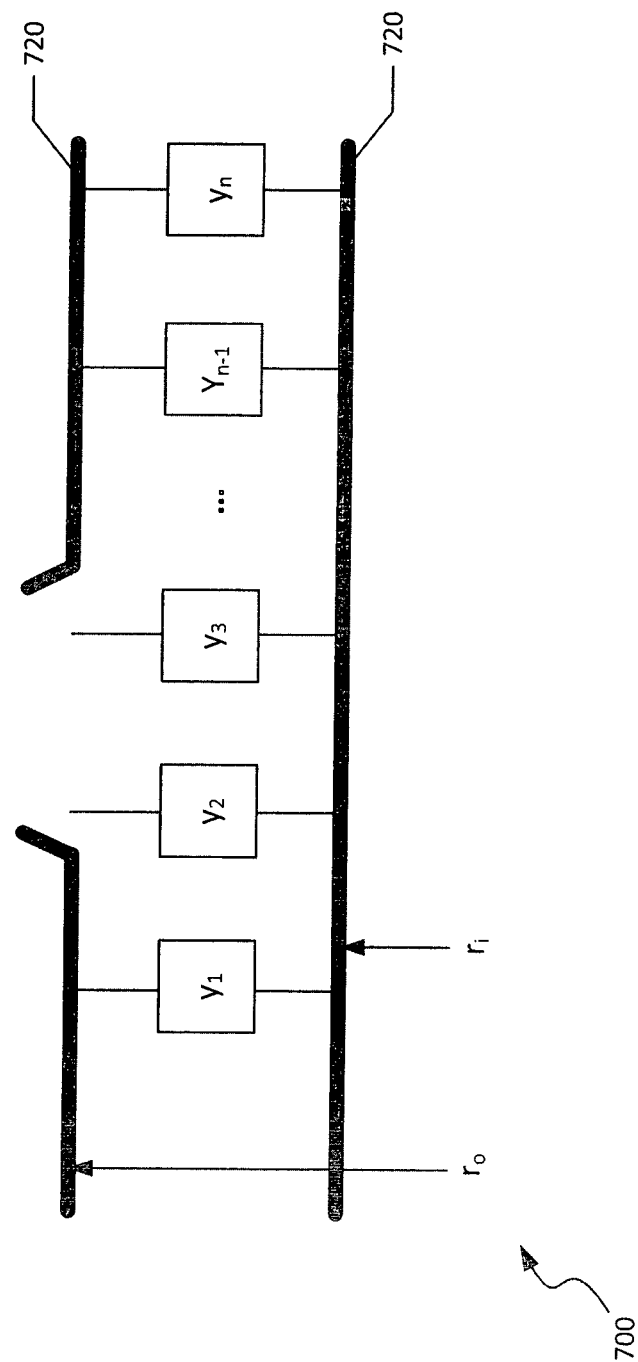
FIG. 13 is a schematic view of the hose assembly of FIG. 10 in the event of a peeloff failure at a particular location, according to an example embodiment.

During normal operation of the hose, the admittance will, similarly to resistance as discussed above, remain constant over time. However, hose characteristics will change over time. This may be modeled as either a failure of the internal conductive layer (e.g., in the case of pressure within the hose weakening the hose from the internal walls outward), or failure of the external conductive layer (e.g., due to compression or peel-off, where a portion of the hose wears or tears away). FIGS. 11-13 represent these differing scenarios.

FIG. 11 illustrates a change in a schematic of the hose assembly 700 in the event of a localized internal failure. In this case, an internal failure results in an increase in the radius $r_i$ of the inner layer 710 at the failure point. This results in the distance between the inner layer 710 $r_i$ and the outer layer 720 $r_o$ decreasing at that point. Accordingly, the local admittance at that point, and therefore the total admittance of the hose assembly, increases.

FIG. 12 illustrates a change in the schematic of the hose assembly 700 in the event of a localized change in the outer layer 720, for example in the case of an object pressing against the outer layer 720. In this case, the outer layer 720 is compressed toward the inner layer 710 in the location of the compression. This results in an increase in capacitance and conductance, due to the narrowing at the wide area. Because an internal point of failure as shown in FIG. 11 is typically in a much more localized position along the hose assembly than a compression of the hose assembly, the overall admittance change in the event of compression is much greater than that of an isolated, internal failure. Typically, it has been observed that the change in overall admittance in the event of external compression of the hose will exceed the overall admittance of the hose, making the two scenarios readily distinguishable. As illustrated in FIG. 12, the compression at unit length admittances $y_2$ and $y_3$ will cause a much greater admittance due to the substantially smaller outer radius across this later area.

FIG. 13 illustrates a change in the schematic of the hose assembly 700 in the event of a localized removal of the outer layer 720, for example in the event of a "peel-off" of a portion of the outer protection of the hose assembly 700. This may occur, for example, due to friction on a hose or cutting through a portion of the outer layers of the hose assembly. As illustrated in this example, the outer layer 720 in the area of unit length admittances $y_2$ and $y_3$ is entirely removed due to the peel-off. As such, the admittance in this area essentially becomes zero. Accordingly, the aggregate admittance will decrease as compared to an original value. This allows the "peel off" effect to be distinguishable as a function of overall admittance as compared to either an internal failure (in FIG. 11) or a compression (in FIG. 12), because in both of those cases admittance increases.

It can be seen that, based on the admittance changes described above, it is possible to track occurrences on a particular hose assembly. For example, a sharp increase in admittance followed by a decrease would represent a compressed hose resulting in a peel-off condition. Additionally, it is possible to determine based on timing of admittance changes whether a failure involves only an internal failure, external failure, or both. Of course in such circumstances a total admittance must be relatively well defined (to be able to distinguish types of admittance changes); in such circumstances, careful hose construction may be required.

Figure 14:
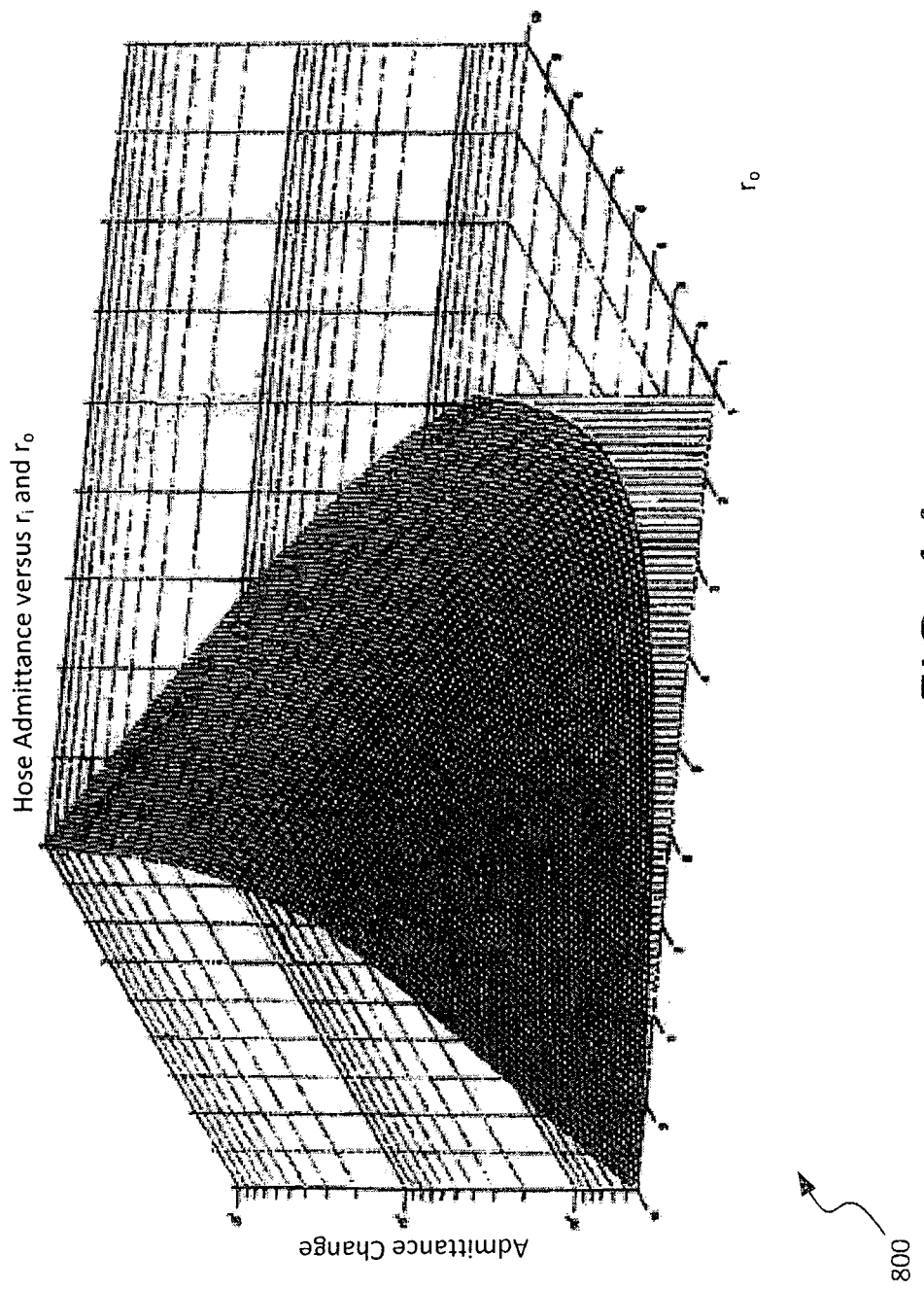
FIG. 14 is a chart illustrating rate of change of admittance based on internal and external layer failures in a hose assembly, according to an example embodiment.

Referring now to FIG. 14, a chart 800 illustrating rate of change and magnitude of change in admittance based on internal and external layer failures in a hose assembly is shown, according to an example embodiment. As illustrated in this chart 800, cumulative hose admittance changes drastically faster and with greater effect based on changes to the external radius (i.e., outer layer 720) as compared to the internal radius (i.e., inner layer 710). These rates of change can be seen in the chart 800, and also are represented by the following equations:

$$\delta y/\delta r_i = k/(\ln(r_o/r_i)^2 r_i)$$

$$\delta y/\delta r_o = k/(\ln(r_o/r_i)^2 r_o)$$

As such, rate of admittance change is slower when $r_i$ increases and $r_o$ remains fixed, rather than when $r_o$ increases and $r_i$ is fixed. Additionally, and as shown in the chart 800, changes to both $r_o$ and $r_i$ will be additive, resulting in even greater rates of change. Accordingly, admittances changes above a threshold value can be determined to be based on an effect on the outer layer, allowing for distinction among types of failures, and occurrences when both types of failures may occur simultaneously.

In connection with FIGS. 10-14, it is noted that, although in the embodiments illustrated admittance is calculated based upon measured resistances and as a function of certain hose characteristics, it is noted that in some additional embodiments, capacitive effects of the hose can be accounted for as well.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A hose degradation monitoring system comprising:
    a hose assembly including a hose having a first conductive layer and a second conductive layer;
    a degradation monitoring circuit configured to detect a resistance of the hose across the first and second conductive layers, the degradation monitoring circuit comprising:
        a voltage source electrically connected to the first conductive layer;
        a resistor electrically connected between the second conductive layer and a ground; and
        a voltage monitoring circuit electrically connected to a location between the resistor and the second conductive layer, the voltage monitoring circuit configured to:
        periodically monitor a voltage at the location;
        determine, in response to the monitored voltage, a resistance attributable to the hose assembly based at least in part on the voltage;
        compute an admittance of the hose assembly associated with each periodically determined resistance; and
        based at least in part on changes to the computed admittance and a rate of change of the computed admittance, detect a possible failure and type of failure of the hose assembly.

2. The hose degradation monitoring system of claim 1, wherein the measurements of the voltage indicate that the resistance of the hose assembly has dropped below the threshold level.

3. The hose degradation monitoring system of claim 1, wherein the voltage source comprises a battery.

4. The hose degradation monitoring system of claim 1, wherein the voltage monitoring circuit is configured to periodically monitor the voltage and a current at the location to determine the resistance of the hose assembly.

5. The hose degradation monitoring system of claim 4, wherein the resistance of the hose is in the range of less than about 1 MΩ.

6. The hose degradation monitoring system of claim 4, wherein the resistor has a resistance of a magnitude sufficient to limit current through the hose assembly below about 0.5 mA.

7. The hose degradation monitoring system of claim 4, wherein the resistor has a resistance of about 400Ω.

8. The hose degradation monitoring system of claim 1, wherein the resistance of the hose assembly is initially in the range of about 10 kΩ to about 1 MΩ.

9. A method of monitoring degradation of a hose assembly having concentric first and second conductive layers separated by an insulating layer, the method comprising:
    (i) applying a voltage to the first conductive layer;
    (ii) measuring a voltage and a current across a resistor connected between the second conductive layer and a ground,
    (iii) determining a resistance attributable to the hose assembly based on the voltage and current measured across the resistor;
    (iv) computing an admittance of the hose assembly based on the resistance attributable to the hose assembly and;
    (v) based at least in part on a rate of change of computed admittances, determining a type of failure in the hose assembly.

10. The method of claim 9, wherein generating an indication of degradation of the hose assembly occurs upon determining that the resistance has crossed the threshold resistance for the plurality of determinations.

11. The method of claim 9, wherein changes in the resistance of the hose assembly increase in precision as the resistance decreases.

12. A method of detecting a type of failure of a hose assembly, the method comprising:
    periodically applying a voltage to a first conductive layer of a hose assembly including first and second conductive layers;
    upon applying the voltage to the first conductive layer, measuring a voltage and a current across a resistor connected between the second conductive layer and a ground;
    determining a resistance attributable to the hose assembly based at least in part on the voltage as measured between the second conductive layer and a ground;
    from each resistance, computing an admittance of the hose assembly; and
    based at least in part on changes to the computed admittance of the hose assembly, determining the existence of a failure in the hose assembly;
    wherein determining the existence of a failure in the hose assembly includes determining a type of failure of the hose assembly based at least in part on a rate of change of computed admittances.

13. The method of claim 12, wherein the first and second conductive layers comprise concentric inner and outer conductive layers.

14. The method of claim 13, further comprising, upon determining that a change in admittance of the hose assembly exceeds a baseline admittance of the hose assembly, identifying a failure in the outer conductive layer.

15. The method of claim 13, further comprising, upon determining that an admittance of the hose assembly has increased from a baseline admittance of the hose assembly, identifying compression of the outer conductive layer.

16. The method of claim 12, wherein computing an admittance of the hose assembly comprises computing the admittance at least in part based on one or more physical characteristics of the hose assembly.

* * * * *